United States Patent [19]

Gregory

[11] Patent Number: 4,881,025

[45] Date of Patent: Nov. 14, 1989

[54] FREQUENCY DEPENDENT IDENTIFICATION OF MATERIALS

[75] Inventor: William D. Gregory, Hannawa Falls, N.Y.

[73] Assignee: Trustees of the Diotec Trust, Canton, N.Y.

[21] Appl. No.: 248,639

[22] Filed: Sep. 26, 1988

[51] Int. Cl.[4] ............................................. G01R 27/26
[52] U.S. Cl. ................................. 324/61 R; 324/57 R; 324/61 P
[58] Field of Search ................. 324/61 R, 61 P, 57 R, 324/57 SS

[56] References Cited

U.S. PATENT DOCUMENTS

| | | | |
|---|---|---|---|
| 3,311,823 | 3/1967 | Benson, Jr. | 324/61 R |
| 3,354,388 | 11/1967 | Perry | 324/61 R |
| 3,815,021 | 6/1974 | Kerr | 324/61 R |
| 4,174,498 | 11/1979 | Preikschat | 324/57 R |
| 4,288,741 | 9/1981 | Dechene et al. | 324/61 R |
| 4,291,708 | 9/1981 | Frei et al. | 324/57 R X |

*Primary Examiner*—Reinhard J. Eisenzopf
*Assistant Examiner*—Robert W. Mueller
*Attorney, Agent, or Firm*—Wall and Roehrig

[57] ABSTRACT

Packaged materials are tested in a capacitive sensor which has plates whose spacing can be accurately adjusted, and whose plates are segmented so that selected segments can be employed. An a.c. voltage is applied across the capacitive plates at accurately known amplitude, phase, and frequency for a number of frequencies. A ratio bridge is tied to each number of frequencies. A ratio bridge is tied to each of the segments and provides outputs that reflect the a.c. voltage and current, both capacitive and ohmic. A zero-crossing detection method or time domain method can be employed to provide precise amplitude and phase, or a quadrature or phase-sensitive detection method can provide amplitude and phase, or a quadrature or phase-sensitive detection method can provide amplitude and phase of the a.c. current through each segment. Values of capacitance, conductance, frequency dependence of capacitance, and frequency dependent of conductance are compared to stored values of a number of known objects of the target class.

18 Claims, 9 Drawing Sheets

FREQUENCY DEPENDENT IDENTIFICATION OF MATERIALS

BACKGROUND OF THE INVENTION

This invention relates to sorting or identification of materials, and more specifically, to non-destructive analysis of an object or container to identify its make-up or contents, based on its dielectric behavior under an oscillating electric field.

All packaged materials can be characterized by an effective electrical permittivity which can be measured as a dielectric constant, and by an effective a.c. conductance. This is true whether the materials inside the package are homogeneous or non-homogeneous. Several techniques and apparatus for nondestructive testing and classification of the objects' materials have been proposed wherein the object is disposed between a pair of parallel capacitor plates, an a.c. voltage is applied to the plates, and the effective capacitance across the plates is measured. Because different materials have different electrical properties, it is theoretically possible to classify the materials into one of two or more categories, e.g., lean or fatty meats, dry or moist soils, explosive or inert baggage contents. Several prior proposals along these lines are described, e.g., in U.S. Pat. Nos. 4,263,511; 4,370,611; 4,433,286; and 4,493,039.

The prior techniques, while showing some promise, tended to overlook factors that prevented optimal operation. For example, the positions of the parallel plates were fixed, so that the interplate spacing could not be adjusted to match closely the thickness of the object. Also, there was no provision for measuring the capacitance across only the effective cross section of the test object. Accordingly, it was impossible to compensate either for bending of the field lines due to the presence of the dielectric (or conductor) between the plates, or for divergence of the electric field lines at edges of the capacitor plates. Also, none of these systems included a bridge circuit that was resistant to inherent d.c. drift. None of them took into account the fact that stray capacitance between the plate and the bridge circuit could introduce unacceptable errors into the regained measurements.

Accordingly, numerous problems with the methods and apparatus so far proposed, i.e., those arising from the non-ideal characteristics of the sensors, have imposed serious problems. These problems include unused air space in between the sensor plates, bending and bulging of the field lines near edges of the sensors and within the objects under test, and non-ideal characteristics of the materials that are used to hold and orient the test objects between the sensors. In addition there is normal, statistical variation of electrical properties from one test object to the next, and there are changes in these properties caused only by the passage of time. Some of the electrical effects of the test object can be masked by quantities of undesired materials in the test object that are buried in more massive amounts of the normal material within the test object. These and other sample-related anomalies continue, with sensor related problems, to further limit or negate the usefulness of the apparatus and technique.

OBJECTS AND SUMMARY OF THE INVENTION

Accordingly, it is an object of this invention to provide a highly accurate and reliable technique for classifying and identifying materials, which overcomes the drawbacks of the prior art.

It is another object of the present invention to provide apparatus and method that avoids adverse effects due to non-ideal characteristics of measuring equipment and accounts for normal variations of the properties of the objects under test.

It is a more specific object of this invention to provide a statistical technique for accurate classification of objects of the same class or similar classes.

The technique of this invention involves comparison of the test results of an object with a statistical record of a plurality of similar known objects. The test object is placed between a pair of parallel capacitor plates which can be accurately adjusted as to the spacing between them. At least one of the plates is configured as an array of independent plate segments that can be employed selectively. Each of the segments is coupled to a respective sensing circuit, which is placed in near proximity to the segment so as to minimize stray capacitance effects between the circuit and the segment.

The test object is placed between the plates, and the moveable plate is adjusted to an accurately known interval so as to minimize the volume of dead air between the plates. Then a series of sinusoidal voltages are applied to the other plate (which can be either segmented or unsegmented), the voltages having accurately known amplitudes, phases, and frequencies. The magnitude and phase of the resulting electric current is measured for each frequency and for each of the selected segments of the one plate. From the current magnitudes and phases, one or more parameters can be calculated, and these preferably include the capacitance, conductance, and the frequency dependence of capacitance and conductance. By comparing the values of the parameters for the test object with those that have been previously stored to represent a plurality of known objects of the desired type, it can be ascertained whether the internal composition of the test object is within an acceptable statistically normal range of the above parameters. The apparatus can operate on either a time domain or a phase domain analysis. One of the capacitor plates travels on rods or rails and is accurately displaced to known intervals. For measuring the effective capacitance and/or conductance for each segment, a ratio bridge has operational amplifiers serving as buffers for first and second outputs. This automatically compensates for any drift.

The above and many other objects, features, and advantages of this invention will be more fully appreciated from the ensuing description of a preferred embodiment, when considered in connection with the accompanying Drawing.

DETAILED DESCRIPTION OF THE PREFERRED EMBODIMENTS

Figure 1:
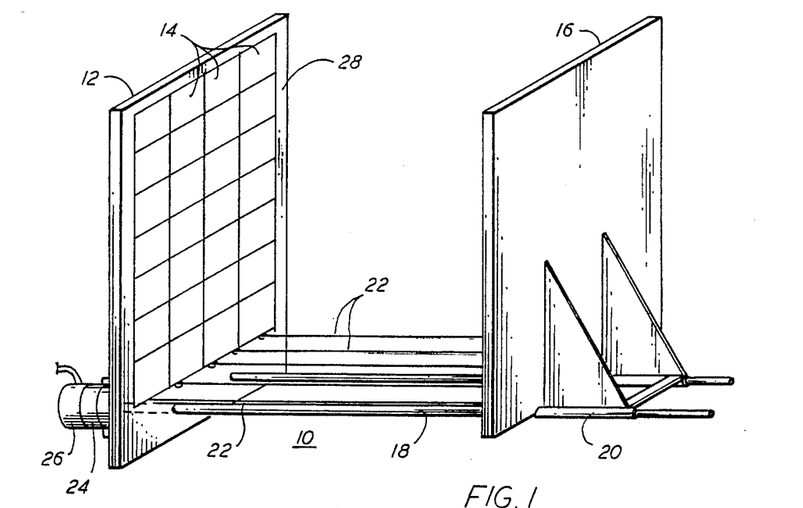
FIGS. 1 and 2 are perspective views of capacitive sensor plate arrangements according to horizontal and vertical embodiments of this invention.

With reference to the drawing, and initially to FIG. 1, a capacitive sensor arrangement 10 into which a test object is to be placed, has a first or fixed capacitor plate 12 in which there are an array of independent segments 14. Preferably, the array is a square grid of these segments, for example, a 64-square grid, eight by eight segments. The particular segments 14 which may correspond to a projection of the test object or to some portion thereof can be selected to avoid edge-effect problems or other effects which may distort the behavior of the device. A second or movable capacitor plate 16 is situated on a horizontal track 18 so that the spacing between the plates 12, 16 can be precisely adjusted. The track 18 is preferably of a low value dielectric material, so as to have a minimal effect on the field lines between the plates 12 and 16. The movable plate 16 has precision linear bearings 20 which slide along the tracks 18. A plurality of platform rods 22 are horizontally disposed between the plates, and these serve to support a test object (not shown) between the two plates 12 and 16. These platform rods 22 should also be of a low value dielectric material to minimize their effect on the field between the plates. A stepper motor 24 and an associated rotary optical encoder 26 can be associated with the plates 12 and 16 for precisely controlling and monitoring the spacing between the plates. For this purpose, one member of the track 18 is threaded to pass through the stepper motor 24 and encoder 26. In addition, on the fixed plate 12 there is a guard ring electrode 28 surrounding the segments 14, and this serves to prevent edge-effect bending of electric field lines for the outer segments 14.

Figure 2:
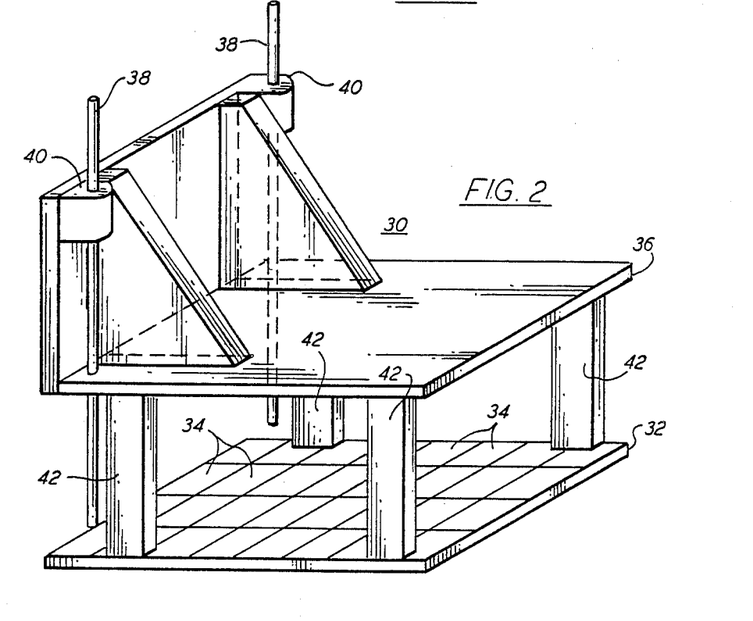

Another capacitive sensor arrangement 30 is shown in FIG. 2. This is a vertical arrangement in which a fixed, lower capacitor plate 32 serves as the platform on which the test object is placed. This first plate is formed as an array of segments 34. An upper movable plate 36 is slidable along vertical tracks 38 and precision linear bearings 40 are provided for this purpose. In this embodiment, there are spacers 42 for establishing a precise spacing between the plates 32 and 36. The spacers 42 should be of a low-dielectric-constant material, and their precise dimensions well known. In this illustrative embodiment, the appropriate spacers 42 can be selected by the operator, and the spacing value can be entered by keyboard. This capacitive sensor arrangement 30 has the advantage that the platform rods of the first arrangement 10 are eliminated. This in turn eliminates the need for correction for their electric effect between the plates.

Figure 3:
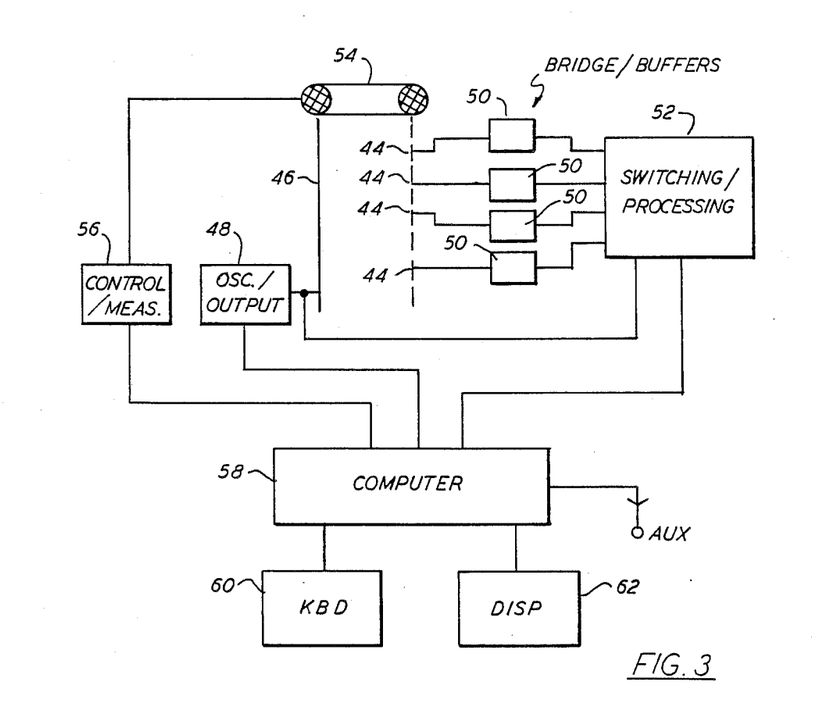
FIG. 3 is a generalized block diagram for explaining the principles of this invention.

A generalized arrangement of the electronics for practicing this invention is shown in FIG. 3. Here, there are two parallel plates including an array of segments 44 and a movable plate 46. These correspond with the pairs of plates 12, 16 or 32, 36 of FIGS. 1 and 2. While only the fixed plate 44 is shown as being segmented, both plates could be segmented.

An oscillator/amplifier 48 provides a.c. voltages at precise amplitudes, phases and frequencies to the fixed plate 46. Each segment 44 of the segmented plate is coupled to an individual bridge/buffer circuit 50 which converts the a.c. current through the capacitive element formed by the test object (not shown) and the parallel plates 44, 46 to an output voltage. The bridge/buffer 50 is preferably a ratio bridge as discussed below with respect to FIG. 8.

A signal switching and processing unit 52 compares the output of the bridge buffer circuits 50 with the driving voltage from the oscillator/amplifier 48, in terms both of amplitude and of phase angle for each frequency that is applied by the amplifier 48. A mechanical plate-adjusting mechanism 54, which controls the position of the movable plate 46, is coupled to a control and measuring circuit 56 which establishes and identifies the precise distance between the plates 44 and 46. This control and measuring circuit 56, as well as the oscillator/amplifier 48 and the switching and processing unit 52, are coupled to a digital computer 58, which has an associated keyboard 60 and display unit 62. The various steps for operating the circuit can be initiated using input from the keyboard 60. The display unit 62 can indicate prompts for an operator to supply further inputs, or to deliver decision information regarding the identification or classification of the test object. Also, other equipment, such as an audible alarm, can be controlled by an output decision delivered over an auxiliary terminal AUX from the computer 58.

There are numerous practical arrangements for realizing the generally described circuit of FIG. 3.

In the more specific description that follows, two analysis techniques are described, and appropriate circuitry is disclosed for carrying out each of those techniques. One technique is the time domain analysis, and is explained with reference to FIGS. 4A-4D. The other technique is the phase sensitive detection method, which is explained with reference to FIGS. 5, 6 and 7.

Figure 4A:
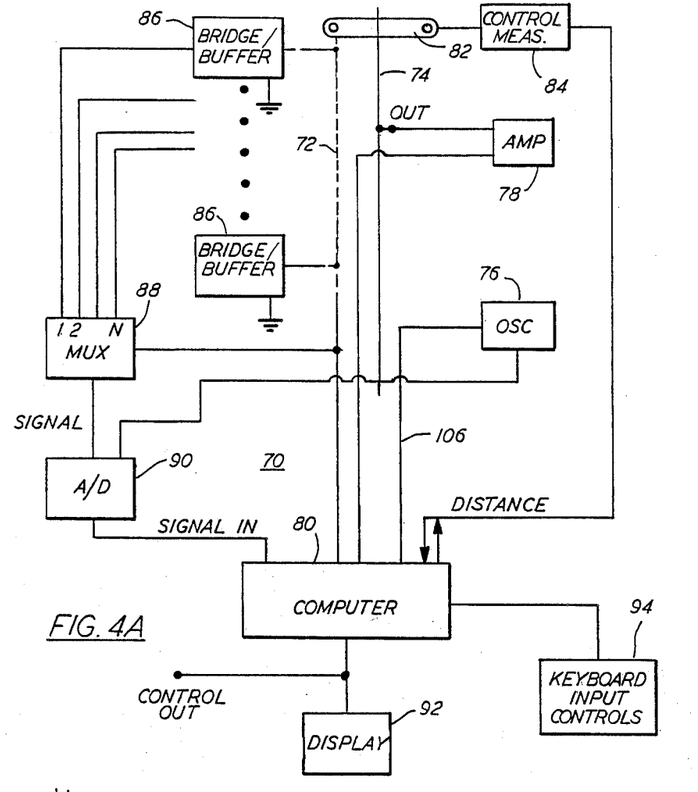
FIG. 4A is a schematic block diagram of circuitry for conducting a time domain technique according to the present invention.

In the time domain analysis apparatus 70, as shown in FIG. 4A, there is a fixed segmented plate 72 and a movable plate 74, which can correspond to the plates 14, 16 of FIG. 1 or the plates 32, 36 of FIG. 2, for example. An oscillator 76 supplies an a.c. wave to the movable plate 74, and the voltage on this plate is then supplied through an isolating amplifier 78 to the computer 80. Plate adjusting mechanism 82, coupled to control and measuring circuitry 84, controls the spacing between the plates 72 and 74. The control and measuring circuit 84 is coupled to the computer 80. For each segment of the segmented plate 72 there is an individual bridge/buffer circuit 86, and each of these has an output which is supplied to a respective input of a multiplexer 88. The multiplex output of the bridge buffer circuits 86 is then supplied to a digitizer circuit 90, which is also supplied with an output from the oscillator 76. A digitized output of the digitizer 90 is then supplied to the computer 80. The computer also is provided with a display 92, a keyboard 94, and a control output.

Figure 4B:
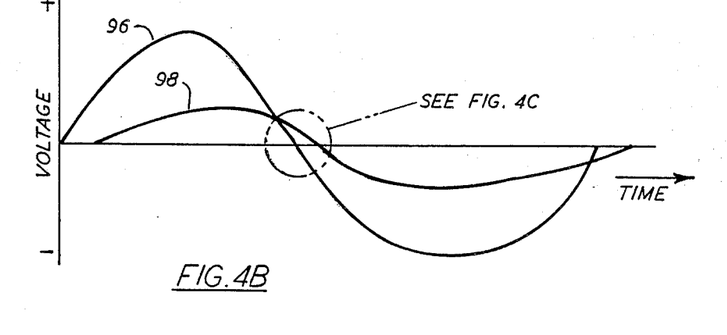
FIGS. 4B, 4C, 4D are waveform traces for explaining the time dependence of applied voltage and sensed current in the embodiment of FIG. 4A.

The computer 80 compares the values of a voltage input waveform 96 and current output waveform 98, as shown, e.g., in FIG. 4B. Then the computer 80 carries out a time-domain analysis, as follows. Basically, the time domain method obtains data on the amplitudes of current and voltage by calculating the slopes of the voltage and current curves 96,98 in the vicinity of the respective zero crossings 100 and 102. The voltage and current will cross the true zero of voltage, but at different times and with different values of slope. The region near the zero crossings is shown in the expanded diagram of FIG. 4C.

Figure 4C:
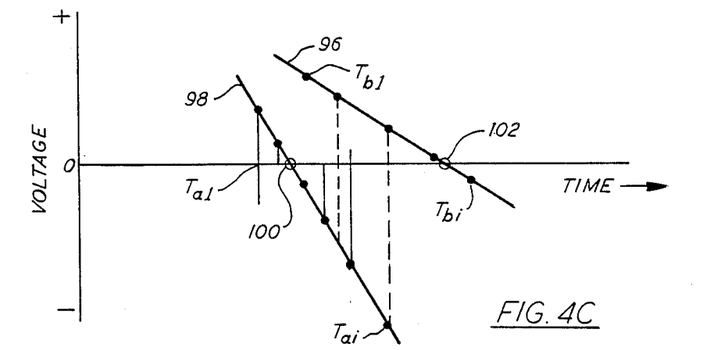

Near the zero crossings, the sinusoid can be well approximated by a linear function as follows:

$$V = A \sin(\omega t) + b$$

where A is the amplitude, $\omega$ is $2\pi$ times frequency, and $\underline{b}$ is a d.c. offset voltage.

This is approximated for small phase differences $$V \approx A \cdot \omega t + b \quad (1)$$

In addition, the difference in phase between two sinusoids near the zero axis can be related to the time difference in zero crossings:

$$\Delta\phi = (t_2 - t_1) \cdot \omega \quad (2)$$

where $\Delta\phi$ is the phase difference and $(t_2 - t_1)$ is the time separation between the two zero crossings 100 and 102.

Where the phase difference $\Delta\phi$ and amplitude $\Delta\phi$ for each of the current and voltage are known, the capacitance and conductance can be calculated from these relationships:

$$\omega C = A_I/A_V \sin(\Delta\phi) \quad (3)$$

$$1/R = A_I/A_V \cos(\Delta\phi) \quad (4)$$

where C is capacitance, 1/R is conductance, $A_I$ is amplitude of the current wave 98 and $A_V$ is amplitude of the voltage wave 96.

These are basically derived as follows (where j is the base of imaginary members, $j = \pm(-1)^{\frac{1}{2}}$):

For a parallel R - C network, the admittance $\widetilde{Y}$ is given as $$\widetilde{Y} = j\omega C + 1/R, \text{ or}$$
$$\widetilde{Y} = \widetilde{I}/\widetilde{V}$$

where  $\widetilde{I} = A \exp(j(\omega t + \Delta\phi))$, and
$\widetilde{V} = A_V \exp(j(\omega t))$ thus: $\widetilde{Y} = \widetilde{I}/\widetilde{V} = (A_I/A_V) \exp(j\omega t + j\Delta\phi - j\omega t)$
$= (A_I/A_V) \exp(j\Delta\phi)$
$= (A_I/A_V)(\cos \Delta\phi + j \sin \Delta\phi)$ thus: $\widetilde{Y} = 1/R + j\omega C = A_I/A_V \cos \Delta\phi + A_I/A_V j \sin \Delta\phi$ The orthogonality of the real and imaginary parts of this yield the relationship of equations (3) and (4).

Therefore, the basic parameters needed for this method of calculating capacitance and conductance are the slopes of the sinusoidal curves near the true voltage zero crossing and the difference in time of the two zero crossings 100,102. These quantities can be obtained by fitting the values of the voltages measured by the apparatus to the expression for the straight line slope. The value of the slope comes directly from the least-squares fit, while the zero crossing time 100 or 102 for each sinusoidal curve 96,98 is obtained by evaluating the bestfit expression at zero true voltage for each sinusoid. This is shown diagrammatically in FIG. 4C. The voltages for each sinusoid are measured at regularly spaced clock times, such as measured time values $T_{a1}$ to $T_{ai}$ for the applied voltage sinusoid and time values $T_{b1}$ to $T_{bi}$ for the output current sinusoid 98.

A standard least-squares fit yields a linear expression valid in the near-zero-crossings regions and also gives the values of the zero crossings at 100 and 102:

Near the zero crossings, the voltage or current value V can be approximated $$V = a_0 + a_1 t, \text{ where } a_1 = A\omega.$$

For each time $t_i$, $$V_i = a_0 + a_1 t_i$$

To produce a least-squares best fit, the sum of square error is minimized, i.e., the residual error $\underline{Re}$ is minimized for some best-fit voltage expression $V_a$.

where $\sum_i (V_i(t_i) - V_a(t_i))^2 = Re$

To minimize Re with respect to $a_0$ and $a_1$, $$\sum_i (V_i(t_i) - V_a(t_i))$$

$$\sum_i (V_i(t_i) - V_a(t_i))(-t_i) = 0$$

or $\sum_i a_o + \sum_i a_i t_i = \sum_i V_i(t_i)$ $$\sum_i a_o t_i + \sum_i a_i t_i = \sum_i V_i(t_i) \cdot t_i$$

If these expressions are taken for some integral number i of samples, the expressions reduce to $$a_0 + a_i \langle t \rangle = \langle V \rangle$$

$$a_o \langle t \rangle + a \langle t \rangle = \langle V \cdot t \rangle$$

where the bracketing "$\langle \rangle$" indicates taking the mean or average of the included value.

These expressions can be solved for a as follows:

$$a_1 = A\omega = \frac{\begin{vmatrix} 1 & \langle V_i \rangle \\ \langle t \rangle & \langle V_i t \rangle \end{vmatrix}}{\begin{vmatrix} 1 & \langle t \rangle \\ \langle t \rangle & \langle t^2 \rangle \end{vmatrix}} \quad (5)$$

or $$a_1 = \frac{(\langle V_i \cdot t \rangle - \langle t \rangle - \langle t \rangle \langle V_i \rangle)}{(\langle t^2 \rangle - \langle t \rangle^2)}$$

As $\omega$ is known, and the values $V_i$ and $t_i$ are easily measured, the value A can be computed by straightforward algorithm.

The zero crossings can be calculated by solving for $$V = 0 = \omega A \cdot t + a_o \tag{6}$$

To use the time domain technique it is necessary to ascertain that the voltages reflective of the a.c. current through each segment and the value of the applied voltage used in computation of capacitance and conductance are in fact the "true" voltages. For these purposes "true" voltage means that the voltage waveform is symmetric about the zero voltage axis. In other words, for the true voltage waveform, the spacing between successive zero crossings is the same for all zero crossings. This is satisfied only if the amplifier outputs as used at various places in the measurement system have no zero frequency output (i.e., zero d.c. offset). However, all practical amplifiers do have offset voltages at the input that are amplified to the output to produce a nonzero d.c. component. Because of this, before the steps described above can be exercised to compute capacitance and conductance by time domain techniques, the output levels must be converted to "true" voltages.

Figure 4D:
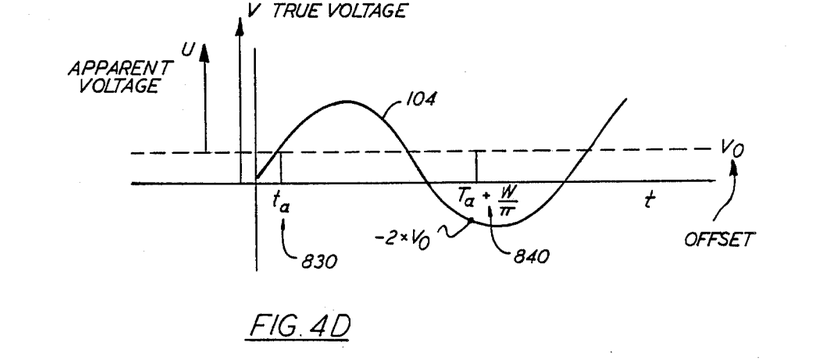

Referring to FIG. 4D, a relatively simple technique can be employed to compensate for d.c. offset. An apparent or measured voltage value U will appear, measured above and below the offset level $V_o$. A sinusoidal wave, as indicated by the waveform 104, will have apparent zero crossings at times $t_a$, $t_a + \tau$, $t_a + 2\tau$, etc. where $\tau$ is the waveform period. There will be intermediate apparent waveform zero crossings also, but these will not be exactly midway between successions of apparent crossings at times $t_a$, $t_a + \tau_i$, etc. If the apparent voltage value U at one-half period after time $t_a$, that is $t_a + \frac{1}{2}\tau$ or $t_a + \omega/\tau$, will be offset below the true voltage zero by an amount equal to twice the offset, i.e., $U(t_a + \omega/\tau) = -2V_o$.

Therefore, simply by measuring this value, an appropriate offset correction voltage $V_{corr}$ can be obtained:

$$V_{corr} = -V_o - \tfrac{1}{2} U(T_a + \omega/\tau) \tag{7}$$

An alternative procedure is simply to employ a least-squares fit algorithm to produce an average value of $V_o$ over a number of cycles, assuming that the true average value of the waveform is zero. This technique provides a higher confidence level for the value $V_o$, especially where the value of the magnitude of the sinusoidal waveform is rather small. However, this is obtained at the cost of increased data acquisition, increased storage requirements in computer memory, and increased requirements for computation time.

Returning to FIG. 4A, it can be understood that the required apparatus to conduct time domain analysis of capacitance and conductance is minimized, and is simple in overall design. The main features are, as previously described, the capacitive sensor formed of segmented or unsegmented parallel plates 72 and 74, the oscillator 76, amplifier 78, bridge/buffer circuits 86, plate moving means 82 and control circuitry 84 and the computer 80 and ancillary equipment. The elements that correspond to the signal processing and switching unit of FIG. 3 include a multiplexer 88 and an analog-to-digital converter 90.

In operation, the oscillator 76 is set to a desired operating frequency by the computer 80 using a frequency control line 106. A trial set of gain values are set by the computer 80 for the amplifiers 86. The computer also selects which segments are to be tested by sending an appropriate set of signals to the multiplexer 88. The A/D converter 90 is then activated, and a series of data points are measured in turn. A reference value indicates the voltage applied to the sensor plates 72,74, while a signal value indicates the current passing through the segment.

If the voltages reaching the A/D converter 90 are too large, or are distorted, or are too small, then a new set of gain values is selected and this process is repeated until the resulting voltage and current curves are similar to those of FIGS. 4B and 4C. It is desired to use as much of the amplifier's dynamic range as is possible, without exceeding a voltage value beyond the useful range of the D/A converter 90, or of the amplifiers. The measurement and calculations proceed as described, in turn for each desired segment. This is repeated until the capacitance and conductance have been measured for all segments of interest for all frequencies of interest.

A phase-sensitive detection (PSD) system, and suitable circuitry, will now be explained with reference to FIGS. 5–7. This technique avails itself of the inherent 90-degree phase difference between capacitive component and ohmic component of the segment impedance, and then employs principles of integration of sinusoidal functions.

For example, if one considers the capacitive and ohmic conductive components of impedance to be a parallel network of a capacitor and a resistor, then the alternating current of frequency $\omega/2\pi$ passing through the segment of interest is given by $$\bar{I} = Vj \sin(\omega t) \times \omega C + V \cos(\omega t) \cdot 1/R, \tag{8}$$

and the voltage across the segment is given by $$\begin{aligned}\bar{V} &= V_m \exp(j\omega t) \\ &= V_m \sin(\omega t) + V_m j \cos(\omega t)\end{aligned} \tag{9}$$

Thus, if the current I is integrated over one period exactly, in terms of the driving signal multiplied or mixed with signals that are either in phase (zero phase shift) or in quadrature (ninety-degree phase shift) with respect to the plate voltage, the integral values that result yield the following quantities which are directly proportional to the capacitance and conductance, respectively:

$$\int_{t=0}^{2\pi/\omega} I(t) \sin(\omega t)\, dt = \omega C/2 = \omega C/2 \text{ and} \tag{10}$$

$$\int_{t=0}^{2\pi/\omega} I(t) \cos(\omega t)\, dt = 1/2R = 1/2R \tag{11}$$

It is a characteristic of the sinusoidal integral that signals at other frequencies and/or other phases than those of the mixing signal will yield a zero result upon integration. Therefore, the problem of discerning between apparent and "true" voltage levels is avoided, and the contribution of possible noise signals at random phases or other frequencies is drastically reduced. Moreover, with this technique the bulk of computation of capacitance and conductance values is performed by analog mixing and integration, so these values can be gathered for many segments at once. The associated computer can be used simply to read and store capacitance and conductance values. It is possible thus to integrate at a rather high rate, as compared to the relatively slow rate of the time domain technique. Thus the useful range of frequencies can be extended where the PSD technique is employed. However, to attain these advantages, the equipment is somewhat more sophisticated and complex than the equipment for the time domain technique.

Figure 5:
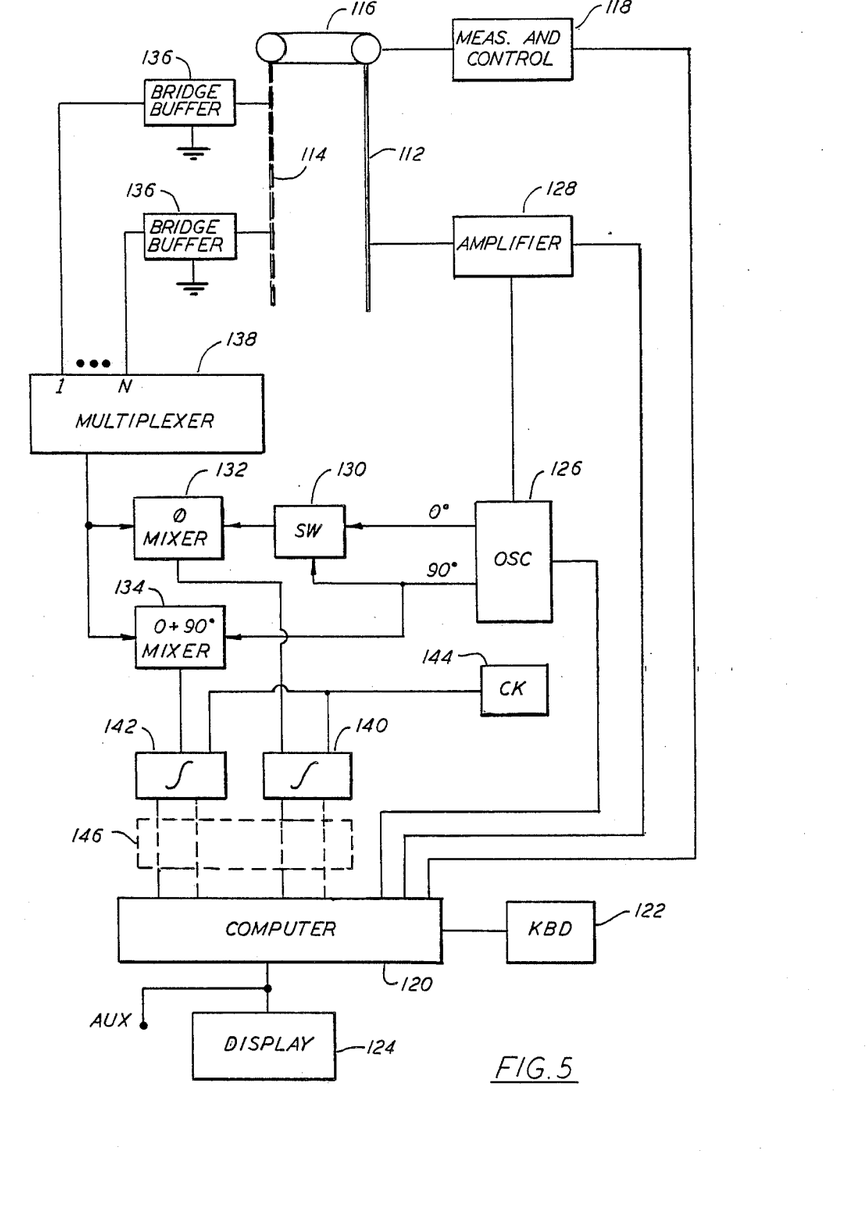
FIG. 5 is a schematic block diagram of circuitry for conducting a segment serial-frequency serial-phase-sensitive detection (PSD) technique according to this invention.

A first embodiment of this invention for carrying out the phase sensitive detection technique carrying out the phase sensitive detection technique is shown in FIG. 5. In this embodiment, and in those that follow, there is a ninety degree phase difference imposed on either the reference waveform or the output waveform for distinguishing between the capacitive and the conductive components of the segment impedance. These two components are then determined by applying basic principles of integration of sinusoidal functions. This view shows a PSD arrangement 110 for carrying out a segment-serial, frequency-serial, PSD technique. Here, there is a movable plate 112 and a fixed, segmented plate 114, with the spacing between the plates being accurately determined by a mechanism 116 coupled to a control and position feedback circuit 118, the latter supplying position information to a computer 120. The computer has an associated keyboard 122 and display 124. An oscillator 126 having a control output coupled to the computer 122 supplies a sinusoidal voltage to an amplifier 128 which is coupled to the fixed plate 112 and also to the computer 120. The oscillator 126 has both zero-degree and ninety-degree phase-separated outputs which are coupled through a switch circuit 130 to a first mixer 132. The ninety degree output is coupled to a second mixer 134. Each segment of the fixed capacitor plate 114 has an associated bridge/buffer circuit 136, whose outputs are fed to respective inputs of a multiplexer 138. A multiplex output is then fed to another input of each of the mixers 132 and 134. The mixer outputs are supplied from the mixer 132 to an integrator 140 and from the mixer 134 to another integrator 142, both of which are controlled by a clock circuit 144. These integrators provide outputs which can be digitized over one wave-form by a digitizer circuit 146 and fed to the computer 120. The digitizer 146 is shown in dotted line, as it can also be incorporated as part of the computer 120.

In this case, the waveform applied by the oscillator 126 and amplifier 128 to the plate 112 is supplied at one discrete frequency at a time, and the bridge/buffer circuits 136 are sampled one at a time, in sequence, for each frequency. Thus, the segments of the fixed plate 114 are polled sequentially, and a signal reflective of the current flowing through each segment is mixed separately in the two analog mixers 132 and 134 with quadrature sinusoidal signals that differ in phase by zero degrees and by ninety degrees, respectively, from the voltage applied to the segment. The outputs of the two mixers are integrated over a precisely determined time interval, with the resultant voltage level being supplied, i.e., as a digital value, to the computer 120. From this information the capacitances, conductances, and frequency dependencies of the capacitances and conductances can easily be computed and stored.

Figure 6:
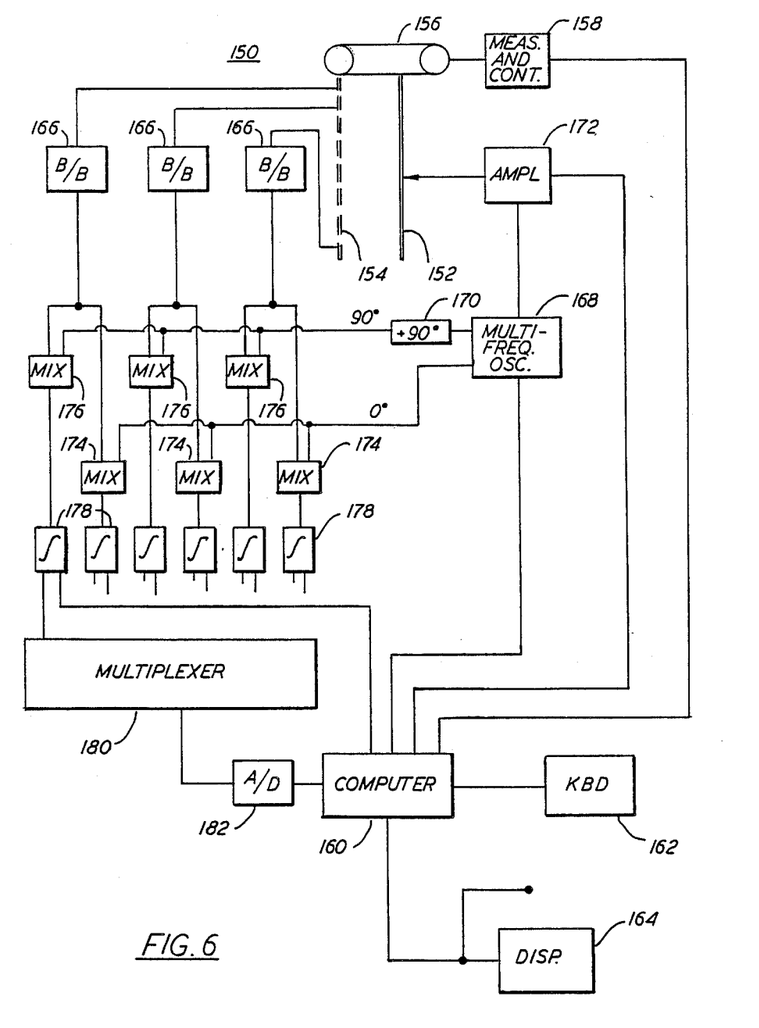
FIG. 6 is a schematic block diagram of circuitry according to another embodiment of this invention for conducting a segment parallel - frequency serial - PSD technique.

FIG. 6 illustrates another possible embodiment of this invention, in this case for practicing a segment-parallel, frequency-serial PSD technique. That is, in the embodiment of FIG. 5, a plurality of segments are polled at any given time, but only one frequency is tested at a time. In this embodiment, a PSD arrangement 150 has a movable plate 152 and a segmented plate 154, and the interplate spacing is adjusted by a mechanical adjustment mechanism 156 that is coupled to a control and measuring circuit 150, which is in turn controlled by and supplies precise spacing information to a computer 160. The computer has an associated keyboard 162 and display 164.

As with each of the previous embodiments, each segment of the segmented plate 154 has an associated bridge/buffer circuit 166. A multi-frequency oscillator 168, coupled by a control line to the computer 160 has a zero-degree output and another output coupled through a ninety-degree phase delay 170 to serve as a ninety degree phase separated reference sinusoid. An amplifier 172 receives the voltage from the oscillator 168 and supplies it at a precisely known amplitude to the fixed plate 152. The amplifier 172 also supplies appropriate amplitude, phase and frequency feedback data to the computer 160.

The outputs of the buffers 166 are each supplied to a respective pair of mixers 174 and 176. Each of the mixers 174 mixes the bridge/buffer circuit output with the zero-degree delay voltage, while each of the mixers 176 mixes the bridge/buffer output with the ninety degree phase separated voltage. The output of the mixers 174 and 176 are all supplied to respective integraters 178, which are controlled, e.g., by the computer 160, to integrate the mixer outputs over a precise time interval, and each then supplies an integrated output through a multiplexer 180 and digitizer 182 to the computer 160.

Figure 7:
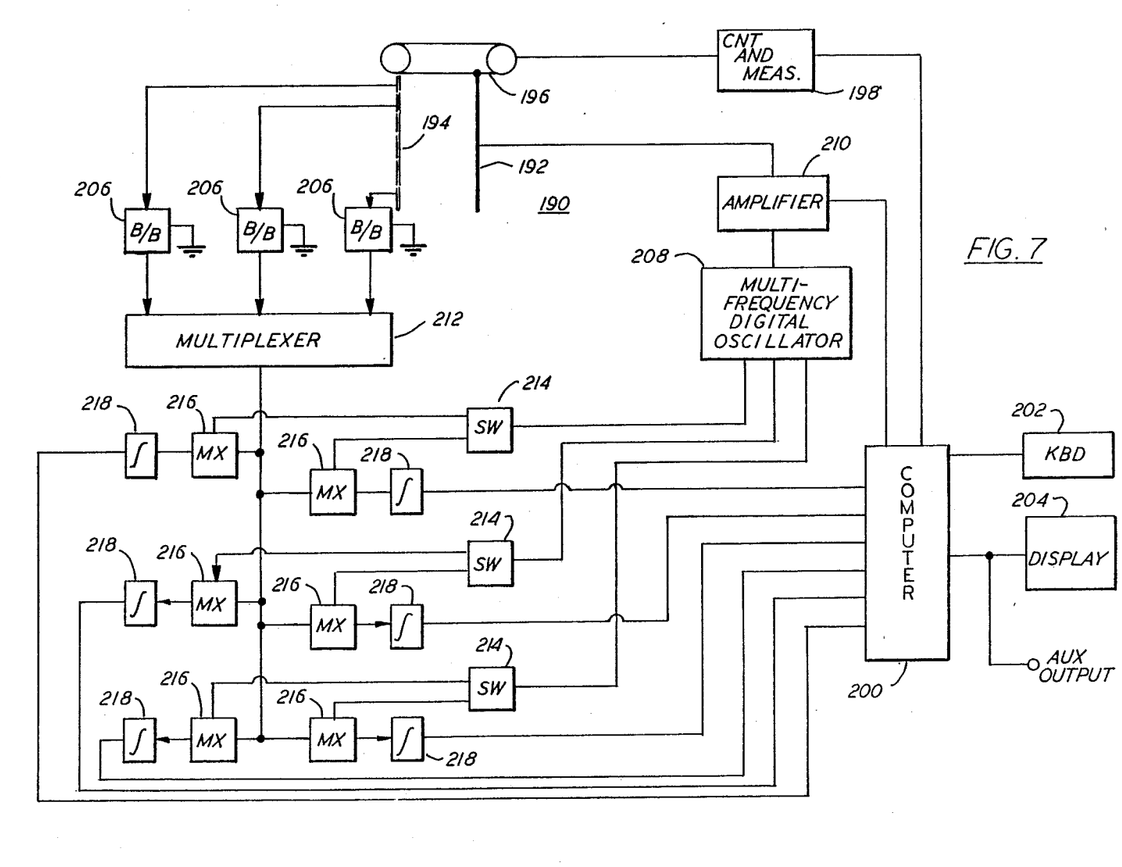
FIG. 7 is a schematic block diagram of circuitry according to still another embodiment of this invention for conducting a segment serial - frequency parallel - PSD technique.

In FIG. 7 there is illustrated yet another embodiment which carries out a segment-serial, frequency-parallel PSD technique. In the embodiment of FIG. 7, a PSD circuit arrangement 190 employs multiple frequencies, but analyzes the segments serially, one segment at a time. In this arrangement 190 a movable plate 192 and a fixed segmented plate 194 are adjustably separated by a mechanical moving mechanism 196, that is coupled to a control and measuring circuit 198, which receives control signals from and supplies feedback signals to a computer 200. The computer 200 has an associated keyboard 202 and display unit 204. As with the previous embodiments, each segment has an associated bridge/buffer unit 206. A multi-frequency digital oscillator 208 furnishes a combined output through an amplifier 210 to the movable plate 192. Thus, the plate 192 is furnished with a driving voltage that is a combination of several sinusoidal voltages, each at a precisely known phase, frequency, and amplitude.

The bridge/buffer units 206 each supply an output to a respective input of a multiplexer 212, which combines these outputs serially and furnishes a multiplexed output signal. The multi-frequency digital oscillator 208 also has a plurality of separate outputs, each supplying a pure sinusoidal wave at a respective discrete frequency to a respective switch circuit 214. From here, separate sinusoidal voltages are supplied, at ninety degree phase separation, to mixers 216. Each mixer 216 supplies a mixed output to a respective integrator 218 which, in turn, supplies a respective integrated value to the computer 200.

In each of FIGS. 5 and 7, the switch 130 or 214 is operated so as to supply the zero degree phase separated waveform to the mixer in operation, and to supply the ninety-degree phase separated signal to the mixer 132 or 216 so as to carry out an internal calibration procedure.

Rather than the specific embodiment shown in FIG. 7, it would be possible, within the constrains of this invention, to obtain capacitance and conductance data at many frequencies for the many segments by employing Fourier transform techniques. To this end, any of several known fast-Fourier or digital-Fourier integrated circuits are commercially available, and could be employed. If one of these fast-Fourier circuits is employed for each segment, all information could be obtained simultaneously for all segments.

Figure 8:
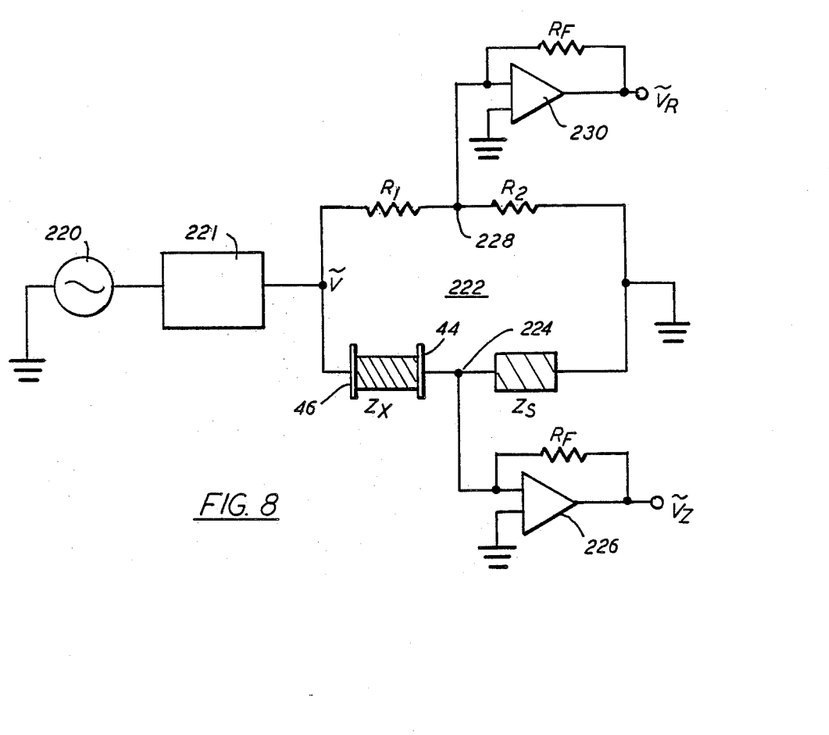
FIG. 8 is a ratio bridge and buffer circuit that can be employed with each segment of the segmented capacitor plate to obtain accurate measurement of the phase and magnitude of the current flowing through the segment.

FIG. 8 shows an example of the bridge/buffer circuit that is preferably employed for obtaining impedance information, i.e., the capacitance and conductance, for each segment. The bridge/buffer circuit shown can be employed as the element 50, 86, 136, 166, or 206, for example, in the above-described embodiments. As shown schematically in FIG. 8, an oscillator 220 provides a sinusoidal waveform through an amplifier 220 to a bridge circuit 222 formed of resistors R1 and R2 and series impedance loads Zx and Zs. Here, the impedance Zx represents the combined capacitive and ohmic load formed by the test object, and the fixed and movable plates for a given segment, such as elements 44 and 46 of FIG. 3. The value of the standard impedance Zs would be selected based on the anticipated value of the impedance Zx, and would usually be a capacitive load. A junction 224 between the impedances Zx and Zs is connected to an input of an operational amplifier 226, which provides an output voltage $\overline{V}_c$. This voltage represents the complete current that flows in the impedance Zx, due to its combined capacitive and ohmic character. A junction 228 between the series resistors R1 and R2 is coupled to an identical operational amplifier 230, which provides a voltage value $\overline{V}_R$, and this voltage level represents the real component of current, i.e., the current that is in phase with the applied voltage.

Both of the operational amplifiers 226 and 230 have identical biasing resistors RF and, to obtain identical operating characteristics, both of these amplifiers 226,230 are contained on a single integrated circuit.

The bridge/buffer circuit of FIG. 8 should be coupled directly and in close proximity to the respective capacitor segment 44, capacitance so as to minimize or eliminate any stray capacitance of the effects of any extraneous fields.

The standard impedance ZS should be selected so as to have approximately the same impedance as that of the segment impedance Zx when the segment has no object under test. The absolute value of the impedance at the input of the amplifier 220 should be such that high-quality characteristics are possible within the amplifier. Once the value of the impedance Zs is chosen, the resistors R1 and R2 are chosen to have approximately the same impedance values as the magnitudes of the impedances Zx and Zs, respectively. With these circuit components, the gains gz and gr of the amplifiers 226 and 230, respectively, can be set to be the same. Because the amplifiers are both part of the same integrated circuit package, they will have virtually identical operating characteristics. Therefore, the phase error that is attributable to these amplifiers will be very close to equal. This permits each phase error to cancel out the phase error due to the other amplifier, if it is the ratio of voltages $\overline{V}_R$ to $\overline{V}_c$ that is employed to compute the segment impedance Z rather than the difference voltage, as is commonly used with other bridge circuits, such as Wheatstone or Maxwell bridges.

The present invention can be better understood from this description of the method of using the apparatus just described. While several exemplary embodiments of this invention may be employed, the methods of use are generally the same for each. Such differences as exist in application of the different embodiments can be discussed as need be.

The first step in using this apparatus is to calibrate standards of capacitance and conductance for objects of the intended class. That is, the apparatus is to be calibrated in terms of the voltage, current, and phase dependence of the capacitive sensor. A significant feature of this invention is that the measurements can be calibrated entirely from a set of measurements on a set of test objects: reference to external standards is required rarely, if at all. Generally, testing against an external standard would be required only after the equipment is first constructed, if the apparatus is altered or repaired, or if components are changed.

One basic feature of the apparatus that permits internal standardization is that the capacitive sensor can serve both as an air capacitor when no test object is present, and as a sample holder and sensor for the test objects. Calibration procedures then must affect these two aspects of the apparatus:

The features of the air capacitor, namely the influence of supporting structure, e.g. rods, which produce capacitances and conductances not quite those of an ideal air capacitor; and the inherent errors due to the amplifiers, integrators, mixers, multiplexers, and other electronic subsystems that may affect the amplitudes and phases of the measured voltages and currents.

The first type of characteristics includes, for example: (1) the bending of field lines because the parallel plate capacitor does not have sufficiently large dimensions compared to the spacing between the plates, (2) the electrical properties of the materials used to cover the capacitor plates and/or to provide a platform allowing the object under test to be held in a reliably established position, (3) electrical energy loss produced by stray electric fields from the capacitive sensor generating currents in the materials surrounding the capacitive sensor, e.g., cabinetry, electronics components and other parts of the apparatus.

The second type of characteristics are generally related to the non-ideal properties of the electronics components comprising the circuitry. Both types of characteristics can change with time due to the effects of temperature, humidity, use and damage, and natural aging of components.

After initial manufacture, or after alteration, the apparatus should be calibrated externally, i.e., against known standards of length, time, voltage, current, and capacitance. The voltages and currents measured by the analog-to-digital converters and other components in the various embodiments can be calibrated against standard voltage and current sources. The characteristic capacitance and conductance of each segment and its associated buffer/bridge circuit can be calibrated against a standard bridge circuit. The spacing between capacitor plates should be accurately measured and the precision linear bearings and tracks can be carefully checked with a precision micrometer. Finally, the timing circuits and oscillator frequencies can be calibrated against standard clocks. These initial calibrations should remain valid for long periods of time (months to years), and the calibration data can be stored in computer memory to be used in the more frequent internal calibrations.

Internal calibrations can be effected generally as follows:

For the time domain embodiment (FIGS. 4A-4D) measurements of change of phase can be reliably obtained from the known frequencies of the applied voltages, and from the timing of the associated analog to digital converters, without further internal calibration.

Voltage offsets Vo of the amplifiers and other components in the apparatus can be compensated for by the method described above for removing offset from the voltage and current waveforms (See FIG. 4D and attendant discussion). For the time domain technique, this portion of the internal calibration is performed every time a measurement is made. The gains and amplitude values of the circuit components and the absolute value of the phase for the oscillator will require internal calibration less frequently. This can be accomplished by moving the capacitor plates to known distances obtained from the external length calibration, and scaling the measured capacitance values to equal the stored values obtained during the external capacitance calibration. Because of the characteristics of the time domain embodiment, this step yields a calibration of the magnitudes of the voltages and currents used to compute the segment capacitances and a measure of the absolute value of the phase (at the value characteristic of capacitance). The conductance of each segments is then immediately calculable from this information, using the externally calibrated values for the change of phase, since the conductance information is exactly ninety degrees out of phase with the capacitance values.

The mathematical expressions for this type of internal calibration are as follows:

$$\tilde{V} = -\tilde{I}R, \text{ and thus} \qquad (12)$$

$$\tilde{Z} = \tilde{V}/\tilde{I} = -\tilde{V}/\tilde{V}_Z R \qquad (13)$$

When using any of the phase sensitive detection embodiments, the voltage offsets caused by the non-ideal nature of the electronics components is calibrated internally by measuring the outputs of the integrator circuits when the output of the oscillator circuits are set to zero. It is necessary to do this internal calibration twice, once for the zero-degree side of the phase sensitive detectors and once for the ninety-degree side. These offset values are then stored in a storage means, e.g., in the computer, and subtracted from all subsequent measurement values to produce true zero output when the oscillator input is zero.

The gains of the circuits must also be calibrated and must be based on information obtained about the absolute value of the oscillator phase. Once again, this information can be obtained from the stored external capacitance calibrations. With the apparatus set normally, the measured capacitance values obtained using the ninety degree reference signal are scaled to fit the externally calibrated and stored sensor capacitance values at the various sensor plate spacing distances. Then the ninety degree reference signal is switched to the mixers normally used for the zero degree component and the process is repeated. In this way, the amplitude of the signals for both phases are calibrated against known capacitances and the phase relationships are properly set using the known phase value for the externally calibrated sensor segment capacitances.

Sensor and test-object related extraneous influences are also minimized or eliminated in the embodiments of this invention. These influences arise because of imperfect characteristics in the capacitive-sensor sample holding arrangement, and generally have four sources:

(1) The electric fields near the edge of a parallel plate capacitor or near the edge of the test objects tend to bend; electrical properties obtained from data taken near such edges cannot be easily analyzed using a parallel-plate capacitor model.

(2) Even away from the edges, the test objects often exhibit an apparent variation of the measured electrical properties that change in a smooth fashion across the object.

(3) The objects under test often do not completely fill the space between the capacitor plates, allowing an air gap between the objects and the sensor plates that must be accounted for in the measurement.

(4) Some means must be used to hold the test objects in place or to keep the operator of the apparatus from undesirable contact with the voltages produced by the oscillators and amplifiers. The materials in these holding means will affect the values of the measured electrical properties.

To reduce the effects of field-line bending, the capacitor sensors are partially segmented and only selected ones of the segmented regions are used for measuring the electrical properties of objects under test. The segmented regions that are more towards the center of the capacitor sensor and bounded by an outer region, held at the same voltage as the segmented region, that is considered the guard ring area. The width of the guard ring region is such that the field line bending occurs mostly in the guard area, and since this area is not included in the measurements, this helps minimize field line bending effects on the measurements. Additionally, field line bending that occurs due to bending near the edges of the object under test can be reduced by not including segments in the measurements that are near the object edges.

The selective use of segments also helps to correct apparent variations of measured electrical properties across the test object. These variations are caused by further field line bending within the test object. By defining each segment as a different region an comparing electrical properties of the object under test to the same regions defined for the class of similar objects that are to be compared to the test object, this spatial dependence is virtually eliminated. To use this feature of the invention, it is best to place the objects under test at the same position each time with respect to the coordinates of the segments. That is, the test objects should be accurately located within the bounds of the same segments each time that type of object is tested. Means are preferably provided in the apparatus to accomplish this.

The air gap problem can be approached in several ways. When possible, the movable plates can be positioned so that the test object touches the plates. In cases where the test objects are of a known and fixed size for all objects of a class, the air gap effect an be eliminated by using a correction stored in the storage means without actually moving the plates to touch the object. For objects of irregular shape that will not completely fill the space between the capacitive sensor plates, or for those cases where the plates should not touch the object, the measurement can be acquired at two or more known separations of the capacitive sensor plates, and the effect of the air gap on the measured properties of the object can be eliminated as a solution to a set of nonlinear equations, using the computer or other calculational means provided for in the apparatus of the invention.

Finally, the effects of the materials used to hold the test objects in place are minimized by methods similar to the methods so far described. Since those materials are in place during the calibration steps, the first order effects of these materials will be absorbed in implicit alterations of the calibration constants. Further effects of these materials will be eliminated by the step of registering each object under test in the same position and comparing the objects under test to the object classes using a segment-by-segment definition of regions within the objects.

For many applications of this invention, materials of interest may be buried within the object under test, or there may be variations within the object. In such cases, the gross capacitance and conductance alone may be difficult to interpret to find the desired material or variation, particularly if it is contained within a small region of the test object.

This difficulty is reduced in part by measuring and comparing test objects with object classes using the spatial regions defined by the capacitive sensor segments. This aspect of the method of use allows one to focus on small portions of the test object and reduce the effects of adjacent "normal" regions that are not of interest. This technique can be used e.g., to identify drug or explosive contraband in luggage, or to detect the presence of a premium toy in a breakfast cereal box.

Figure 9:
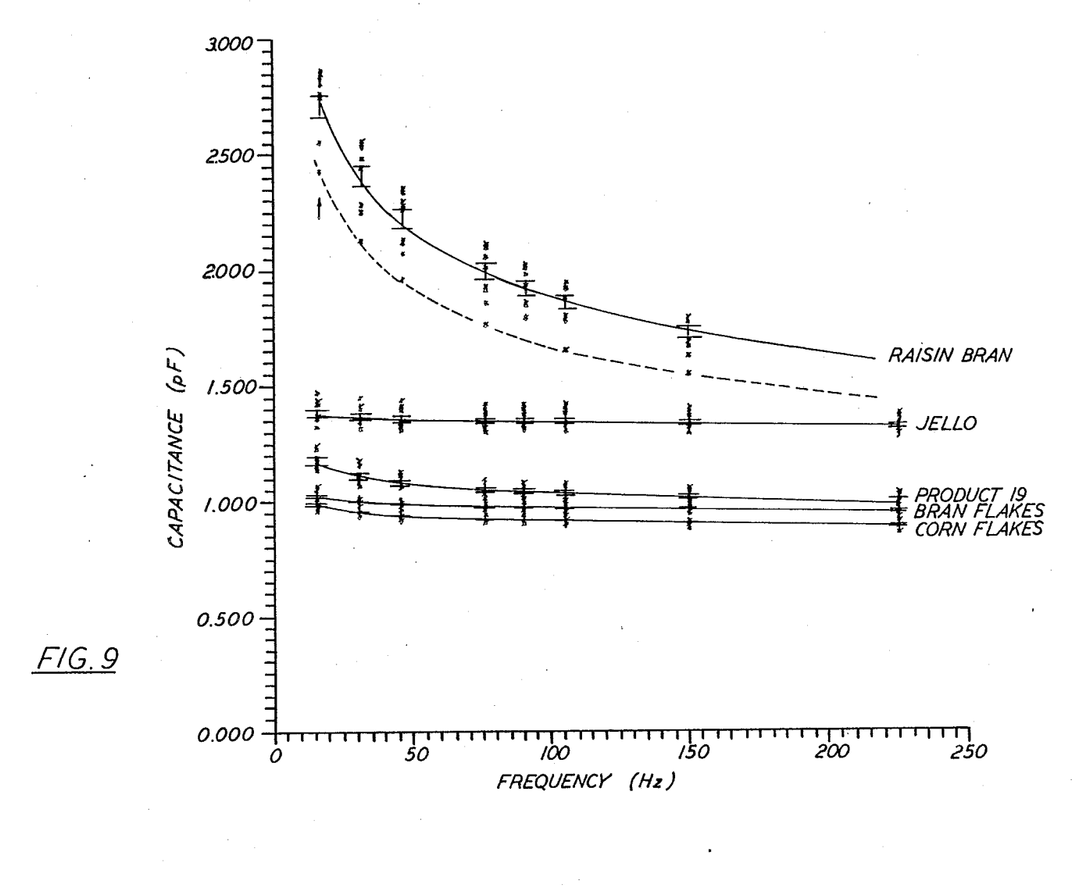
FIGS. 9 and 10 are charts showing the frequency dependence of capacitance and conductance, respectively, for various classes of materials which are to be identified in the apparatus of this invention.
Figure 10:
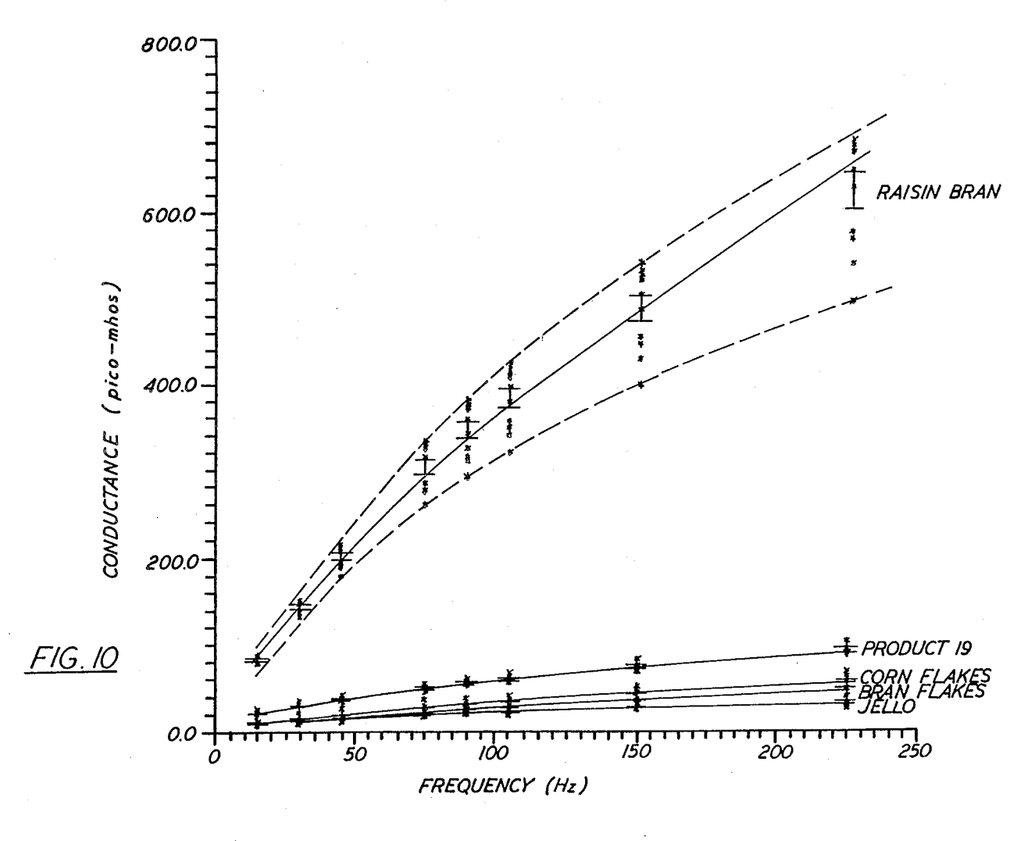

Further separation of buried materials or variations can be obtained with the previously described apparatus to analyze the dependence of the capacitance and conductance on the applied frequencies. With reference to FIGS. 9 and 10, a number of samples, i.e., boxes) of each of a variety of breakfast cereal were tested on apparatus of FIG. 4A, and the results for each cereal box were stored in the computer and plotted. FIG. 9 shows the value and slope of capacitance versus frequency while FIG. 10 shows the value and slope of conductance versus frequency. The frequency in each case is at intervals in the range of up to about 225 Hz. The cereals included corn flakes, bran flakes, "Product 19", and raisin bran flakes; additionally, another packaged comestible (Jello) was among the tested boxes.

As is apparent, each type of cereal has a characteristic capacitance and conductance curve, within a range of normal values. Some variance is to be expected because of factors such as settling during shipment, age of the product, relative humidity of the product, and a variety of other factors. In FIGS. 8 and 9, each individual sample box or test object will follow a similar curve of conductance or capacitance versus frequency as indicated in FIG. 9 by the dash line curve under "raisin bran". Therefore, the quality or identity of product within a given cereal box can be verified by comparing it with the rate of change of conductance or capacitance with frequency as derived from a previously tested sample set comprises of a number of similar boxes of the same breakfast cereal.

As there is some permissible variance of conductance and capacitance, as well as permissible variance of rate of change of these parameter with frequency, a normal or acceptable range of all four of these parameters is established, at each test frequency, using conventional statistical considerations. Each case will have a mean and standard deviation for each parameter.

It has also been found that if a high interest or contraband substance, such as an explosive, is concealed in some boxes of a large, random selection of boxes, the particular boxes can be identified rather readily because the explosive material will have a characteristic frequency dependence for conductance and capacitance. Where the material is concealed in one small portion of the box, the segment-by-segment analysis that is accomplished with this invention will distinguish the explosives-containing parts of the box contents from other, inert contents.

The apparatus previously described permits computation of the frequency derivatives of the capacitance and conductance data. As the measurements are made at multiple frequencies, the capacitance and conductance values can be fit by least squares techniques using the computer, and the derivatives can be obtained from the derivatives of the fit polynomials as follows:

For each segment, the capacitive reactance $$\omega C = (A_I/A_V) \sin(\Delta\phi), \text{ and}$$

the conductance $1/R$ can be given as $$1/R = (A_I/A_V) \cos(\Delta\phi).$$

Any given variable can be expressed as a polynominal series, e.g, for capacitance $C(f)$, $$C(f) = \sum_m a_m f^m; \quad (14)$$

and its derivative $C'(f)$ will be $$C'(f) = \sum_m m \cdot a_m \cdot f^{(m-1)}. \quad (15)$$

Conductance $(1/R)(f)$ can be expressed similarly, giving the frequency derivative:

$$(1/R)' = \sum_m m \, b_m \cdot f^{(m-1)}. \quad (16)$$

These values can be obtained for given pairs of frequencies, $f_i$ and $f_{i+1}$, and the values of the frequency derivatives of the capacitance $C$ and conductance $(1/R)$ calculated taking numerical differences, e.g. for capacitance $C$, $C'(f_i)$ becomes $$C'(f_i) = \frac{C(f_{i+1}) - C(f_i)}{f_{i+1} - f_i} \quad (17)$$

and for conductance $1/R$, $(1/R)'(f_i)$ becomes $$(1/R)'(f_i) = \frac{(1/R)(f_{i+1}) - (1/R)(f_i)}{f_{i+1} - f_i} \quad (18)$$

Higher order derivatives can also be computed in a straightforward manner.

A significant feature of this invention is its ability to supply reliable, optimized decision criteria for identifying objects that are members of a class and those that are nonmembers of that or a similar class. This is accomplished by reducing or eliminating the effects of extraneous influences and erroneous variations of the measured electrical parameters as described hereinabove, and also by reducing the effects arising from internal variations within the test objects, due to packing factors, etc. That is, in a granular or particulate material (such as breakfast cereal, laundry detergent, soils, etc.) there can be normal chemical and physical variations in a class of similar objects, in moisture content, or in orientation of particles within a box. The effects of these factors be minimized as follows:

(1) By using certain selected ones of the measured parameters to correct for variations in others of the parameters;

(2) By minimizing errors statistically, i.e., choosing those parameters that have the greatest difference as between members and nonmembers of the class in question, and then employing a statistical weighting algorithm to favor those parameters that show the most significant difference; and (3) Recording the changes over time of selected individual sampled test objects, so that weighted decision parameters can be identified to best differentiate between members and nonmembers as opposed to class members with differing age factors.

A twofold approach has been found useful for performing the functions of this step. Using the storage, computational, display and interactive means described as part of the apparatus of this invention, the user of the invention can sort the parameters that belong to each of the three classifications just listed, in an interactive mode. The storage and computational means can then be used to quantitatively determine the statistical parameters for decision making and assign weights thereto, in an automated mode. In many cases, it is useful to use the interactive modes and automated modes in succession more than once to achieve complete optimization of the decision process.

Referring again to FIGS. 9 and 10, the curves illustrate the electrical parameters of objects that were tested using this invention. The data are capacitance and conductance of sensor segments for boxes containing granular food materials, i.e., breakfast cereals. Such materials are loosely packed and can have a range of packing densities depending on prior history, i.e., storage and handling for the mot part. Data are shown for many measurements on the substantially identical boxes, wherein the packing differs from one measurement to the next. One can see that the electrical parameters for the several measurements span a rather broad range of values at each frequency, caused by this variation in packing factor. However, it is also clear that for any one such measurement (any one packing factor) the data follow a path from frequency to frequency that is much less broadly spread than the data at any one frequency considered alone. This observation, obtained by using the interactive computational and display features of the invention apparatus, then produces an automated calculation of the parameters (capacitance and conductance) at other frequencies based on the use of these data at one frequency to predict which of the family of curves is appropriate to the instant packing factor.

While this invention has been described in detail by reference to selected preferred embodiments, it should be understood that these serve as examples of the underlying principles of the invention, but that the invention is not to be limited only to these embodiments. Rather, many modifications and variations thereof would be apparent to those of skill in the art without departing from the scope and spirit of this invention, as defined in the appended claims.

What is claimed is:

1. A method of non-destructively identifying and assaying the make-up of a test object by comparison with a statistical record of a plurality of similar known objects by use of a capacitance sensor having a pair of parallel plates which have an adjustable spacing therebetween which can be established at accurately known intervals, and at least a first of the plates being configured as an array of independent plate segments which can be selectively employed, each of the segments being coupled to respective means to sense a current thereat at an accurately measured phase and frequency, the method comprising the steps of placing said test object between said parallel plates, accurately adjusting the spacing between said plates to correspond with a thickness dimension of the object, and selecting the appropriate ones of said segments to correspond with a cross section of the object;

applying a plurality of sinusoidal voltages each of an accurately known amplitude, frequency, and phase, to the other plate of said capacitive sensor;

accurately measuring magnitudes and phases of the electric currents in each of said selected segments of the first of the plates for the applied sinusoidal voltage of each said frequency;

from said measured electric current magnitudes and phases, calculating one or more parameters including at least one of the capacitance, conductance, frequency dependence of capacitance, and frequency dependence of conductance for said test object; and comparing said calculated parameters for the test object with stored values that represent a statistically normal range of such parameters that characterize a plurality of known objects similar to said test object.

2. A method according to claim 1 further comprising the step of establishing said stored values of known similar objects, by performing said steps of placing, applying, accurately measuring and calculating for each of a multiplicity of said similar objects.

3. A method according to claim 1 further comprising performing said steps of placing, applying, accurately measuring, and calculating for a multiplicity of known test objects of at least one other type.

4. A method according to claim 1 wherein said electric currents are measured sequentially for the respective selected segments, by measuring the time dependence of the current for each segment and each frequency.

5. A method according to claim 1 wherein said electric currents are measured sequentially for the respective selected segments, by mixing an output voltage from each said segment with a sinusoidal reference voltage in phase with the applied sinusoidal voltage and with another sinusoidal reference voltage shifted therefrom by 90 degrees, to provide respective mixed outputs, integrating each said mixed output over a predetermined time interval, and computing from the integrated results values of capacitance and conductance for the associated segment at the respective frequency.

6. A method according to claim 1 wherein said parallel plates are held out of contact with said test object while applying said sinusoidal voltage to said other plate of said capacitive sensor.

7. A method according to claim 1 wherein said step of applying said sinusoidal voltages includes applying sinusoidal voltages of discrete frequencies at intervals within a predetermined range.

8. A method according to claim 7 wherein said predetermined range is up to about 225 Hz.

9. Apparatus for non-destructively identifying and assaying the make-up of a test object by comparison with a statistical record of a plurality of similar known objects, comprising a capacitance sensor which includes a pair of parallel plates, at least one of the plates being configured as an array of independent plate segments which can be selectively employed, means mounting said plates permitting adjustable spacing therebetween to selected accurately known intervals, and a plurality of a.c. current sensing means, each coupled to a respective one of said segment for sensing a.c. current thereat at an accurately measured phase and frequency;

a signal generating means for applying to the other of said plates a plurality of sinusoidal voltages each of an accurately known amplitude, frequency, and phase;

means for accurately measuring the amplitudes and phases of the electric currents sensed by said a.c. current sensing means for the applied sinusoidal voltage for each said frequency;

and means for calculating from said measured electric current amplitudes and phases one or more parameters including the capacitance, conductance, frequency dependence of capacitance for the test object between said capacitor plates, and thereafter comparing said calculated parameters for said test object with stored values that represent a statistically normal range of said parameters that characterize the plurality of known objects similar to said test object.

10. Apparatus according to claim 9, wherein said plates are vertically oriented and said means mounting said plates includes a horizontal track on which one of said plates is slidably mounted.

11. Apparatus according to claim 10, wherein said track is of a dielectric material of low dielectric constant.

12. Apparatus according to claim 10, wherein said track includes a threaded rod and has thereon an associated rotary encoder which outputs a signal whose value is indicative of the spacing between said plates.

13. Apparatus according to claim 9 wherein said plates are horizontally oriented and said mounted includes means for accurately adjusting the position of an upper one of said plates.

14. Apparatus according to claim 9 wherein each of said a.c. current sensing means includes a ratio bridge having one input to which said sinusoidal voltages are applied, another input coupled to the associated segment of said one plate, a bridge network of known-value impedances, a first amplifier of predetermined gain having an input connected to an output of said bridge network, and a second amplifier of predetermined gain having an input coupled to said other input of the ratio bridge.

15. Apparatus according to claim 14 wherein said first and second amplifiers include respective operational amplifiers both carried on a common integral circuit.

16. Apparatus according to claim 9 wherein said current sensing means each are disposed immediately adjacent the associated plate segment, so as to minimize effects of stray capacitance between said segment and the associated current sensing means.

17. Apparatus according to claim 9 wherein said accurately measuring means includes a switching and processing circuit having a plurality of inputs respectively coupled to said a.c. current sensing means, an output connected to said calculating means, and a signal input coupled to receive said sinusoidal voltages from said signal generating means, said switching and processing circuit comparing the amplitude and phase of the electric current from the a.c. current sensing means with those of the sinusoidal voltages from the signal generating means.

18. Apparatus according to claim 9 wherein said accurately measuring means includes a first mixing circuit for mixing the electric current from said a.c. current sensing means with the associated applied sinusoidal voltage; phase shifting means for analyzing a 90 degree phase shift to one of said a.c. current and said applied sinusoidal voltage; a second mixing circuit following said phase shifting means for mixing said electric current and said sinusoidal voltage phase-shifted by 90 degrees, and integrating means for integrating the outputs of said first and second mixing means over one period of the applied sinusoidal voltage.

* * * * *